(12) United States Patent
Schneider et al.

(10) Patent No.: US 7,793,795 B2
(45) Date of Patent: Sep. 14, 2010

(54) LIQUID STORAGE AND DELIVERY ASSEMBLY

(75) Inventors: David B. Schneider, Ashland, MA (US); Peter G. Lavigne, Upton, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1126 days.

(21) Appl. No.: 11/384,461

(22) Filed: Mar. 20, 2006

(65) Prior Publication Data

US 2007/0215615 A1    Sep. 20, 2007

(51) Int. Cl.
*B65D 6/28* (2006.01)

(52) U.S. Cl. .............. 220/4.27; 220/4.26; 126/204; 126/263.01

(58) Field of Classification Search ............... 220/4.26, 220/4.27; 126/204, 263.01, 263.05; 222/143
See application file for complete search history.

(56) References Cited

U.S. PATENT DOCUMENTS

| | | | | |
|---|---|---|---|---|
| 385,257 A * | 6/1888 | Ehle | ................................ | 220/8 |
| 687,619 A * | 11/1901 | Couse | ........................... | 312/35 |
| 3,719,272 A * | 3/1973 | Bodine et al. | ............... | 206/701 |
| 4,094,300 A * | 6/1978 | Young | ......................... | 126/677 |
| 4,186,746 A * | 2/1980 | Byler | .......................... | 607/114 |
| 4,428,145 A * | 1/1984 | Wheeler | ......................... | 43/55 |
| 4,598,832 A * | 7/1986 | Alonso | ............................ | 215/6 |
| 4,616,752 A * | 10/1986 | Ridgley | ......................... | 206/533 |
| 5,062,269 A * | 11/1991 | Siegel | ............................... | 62/4 |
| 5,101,804 A * | 4/1992 | Cohn | ..................... | 126/263.01 |
| 5,224,349 A * | 7/1993 | Siegel | ..................... | 126/263.05 |
| 5,355,869 A * | 10/1994 | Pickard et al. | .......... | 126/263.01 |
| 5,443,056 A * | 8/1995 | Smith et al. | ............. | 126/263.05 |
| 5,517,981 A * | 5/1996 | Taub et al. | .............. | 126/263.01 |
| 5,535,908 A * | 7/1996 | Sheu | .......................... | 220/4.27 |
| 5,975,335 A * | 11/1999 | Witenhafer | ............. | 220/592.05 |
| 6,059,146 A * | 5/2000 | Meisner et al. | ........... | 222/145.1 |
| 6,269,980 B1 * | 8/2001 | Randall et al. | ............ | 222/145.5 |
| 6,341,602 B1 * | 1/2002 | Fulcher | .................. | 126/263.07 |

* cited by examiner

*Primary Examiner*—Nathan J Newhouse
*Assistant Examiner*—Christopher B McKinley
(74) *Attorney, Agent, or Firm*—Vincent J. Ranucci

(57) ABSTRACT

A water storage and delivery assembly includes stackable compartments, each compartment having a planar bottom wall, opposed side walls, and opposed end walls, forming a reservoir. Frusto-conically shaped conduits having open large first ends are fixed to peripheries of openings in the bottom walls, and open smaller second ends are disposed below upper edges of the side and end walls. The assembly further includes a bottom-most compartment of the same construction but having no openings in the bottom wall thereof. Water poured into a first conduit is flowable through a plurality of first conduits to the bottom-most compartment while air escapes upwardly through a series of second conduits, the water rising until all the compartments of the assembly are filled. Each compartment is provided with an outlet operable to permit the water to travel from a compartment to an exothermic mass.

12 Claims, 4 Drawing Sheets

LIQUID STORAGE AND DELIVERY ASSEMBLY

STATEMENT OF GOVERNMENT INTEREST

The invention described herein may be manufactured and used by the U.S. Government for governmental purposes without the payment of any royalty thereon.

BACKGROUND OF THE INVENTION

1. Field of the Invention

The invention relates to assemblies for storing liquids, such as water, in a plurality of segregated compartments, and for discharging the liquid from the compartments as needed for activation of masses of liquid activated material. More specifically, the assembly is adapted to store water for delivery to exothermic masses, such as magnesium-iron powder, for the generation of heat.

2. Description of the Prior Art

Water-activated warming devices are known in the art, the devices providing an exothermic reaction over a period of time for purposes such as warming the body of a user. In one known embodiment, water is added to magnesium-iron powder to initiate a rapid exothermic reaction which produces heat, along with magnesium hydroxide and gaseous hydrogen.

Typically, the exothermic material used is disposed in segmented chambers in stacked arrangement, each having therein a material which reacts exothermically with water. The segmentation facilitates controlled, useful heat production over an extended period of time.

However, the water supply is usually concentrated in one area. Various delivery systems have been developed to distribute the water in proper quantities to each of the stacked segmented chambers holding the exothermic material.

There is a need for a water storage and delivery system which is relatively simple in construction and easily transportable and operable to activate a stack of exothermic chambers, either serially or simultaneously, by delivering the correct amount of water to each chamber.

SUMMARY OF THE INVENTION

An object of the invention is, therefore, to provide a water (or other liquid) storage and delivery assembly including a plurality of stacked compartments, each holding, and able to selectively deliver, to an associated exothermic chamber, a correct amount of water to energize the material therein.

With the above and other objects in view, a feature of the present invention is the provision of a liquid storage and delivery assembly including at least two stackable compartments, each being provided with a planar bottom wall, opposed side walls, opposed end walls and, in all but the topmost compartment, a planar top wall, forming the compartment for retaining liquid. At least two frusto-conically shaped conduits are mounted on the bottom walls of the compartments, the larger ends of the conduits being fixed to the bottom wall, and the smaller ends of the conduits being disposed in a plane removed from the plane of the top of the compartment. The bottom wall of a lowermost one of the compartments is closed, and the bottom walls of upper ones of the compartments are provided with openings therein in communication with the larger ends of the conduits mounted in the upper compartments. The top walls of compartments, beneath the uppermost compartment, are provided with orifices aligned with the smaller ends of conduits immediately therebeneath. Liquid admitted to the uppermost compartment by way of the smaller end of a first conduit therein, is flowable through the first conduit of the uppermost compartment and thence to and through lower compartments to overflow the first conduit of the lowermost compartment to fill the lowermost compartment, air escaping from the lowermost compartment through the second conduits. The compartments are filled progressively upward until the uppermost compartment is filled. Each of the compartments is provided with an outlet operable to permit liquid to flow from each of the compartments simultaneously, or serially.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DESCRIPTION OF THE PREFERRED EMBODIMENTS

Figure 1:
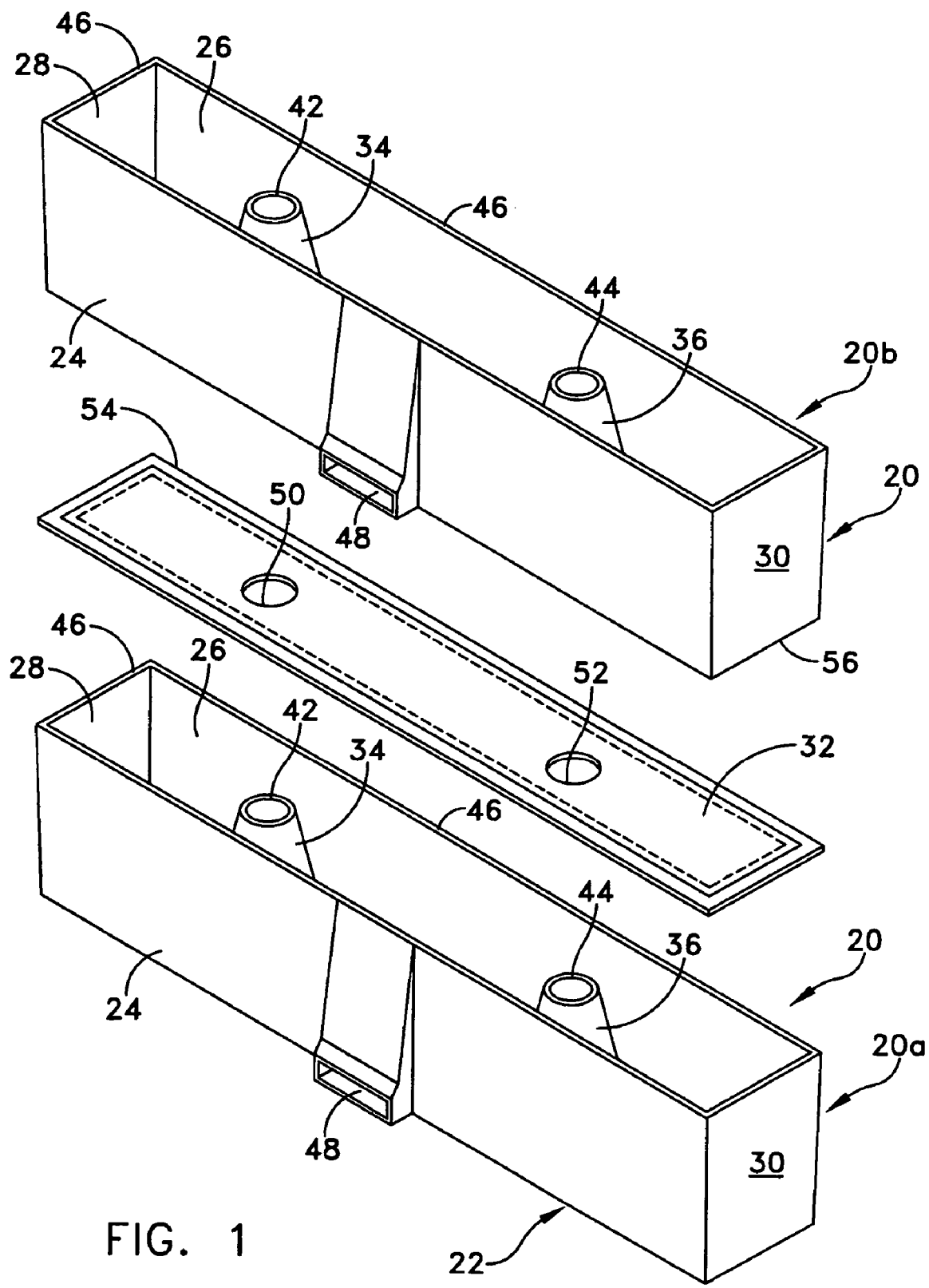
FIG. 1 is a diagrammatic perspective view of two illustrative compartments for a water storage and delivery assembly.

Referring to FIG. 1, it will be seen that an illustrative compartment 20 includes a planar bottom wall 22, opposed side walls 24, 26, opposed end walls 28, 30, and a substantially planar top wall 32.

First and second frusto-conically shaped conduits 34, 36 are fixed at their larger openings 38, 40 (FIG. 3) to the bottom wall 22 and are provided with smaller openings 42, 44 disposed in a plane slightly removed from the plane of the side wall and end wall upper edges.

Each compartment 20 is provided with an outlet 48 disposed in a wall of the compartment proximate the bottom wall 22 of the compartment. The outlet 48 may be an opening covered with an adhesive strip, or the like.

Figure 2:
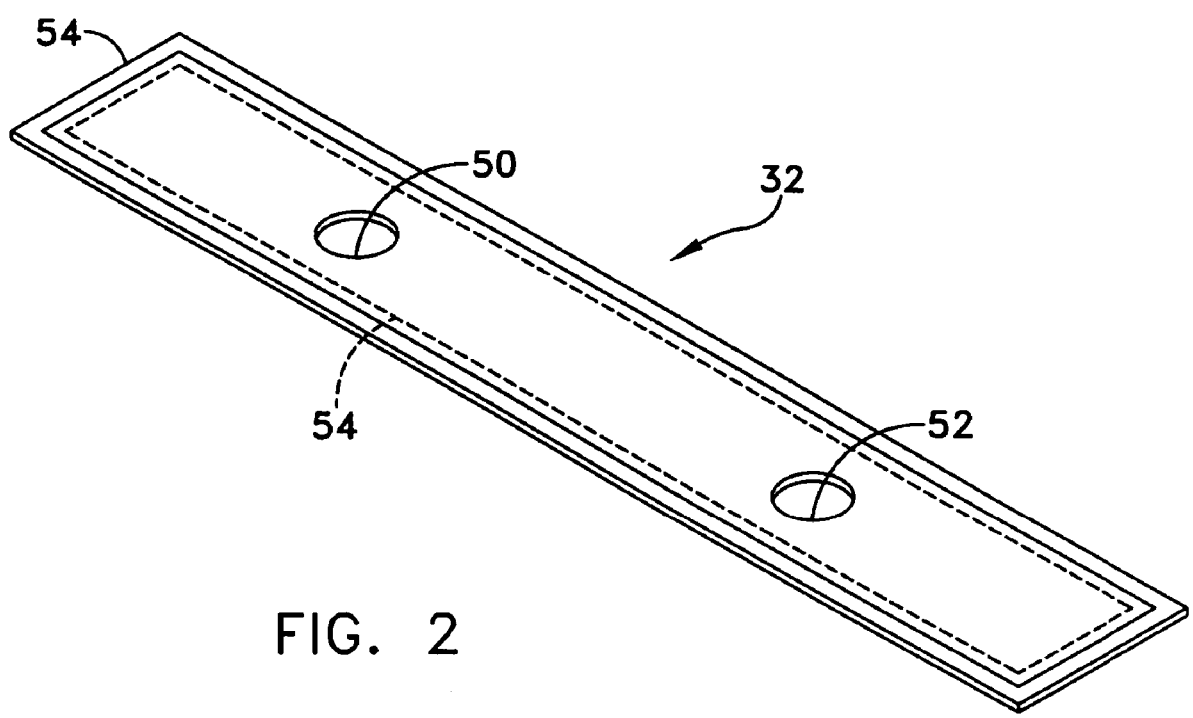
FIG. 2 is a perspective view of a top member for use in conjunction with the upper compartment of FIG. 1.

The top wall 32 (FIGS. 1 and 2) is provided with apertures 50, 52 aligned with the conduit smaller openings 42, 44 and centrally of the conduit larger openings 38, 40. The top wall 32 preferably is provided with grooves or ridges 54 on upper and/or lower surfaces thereof to facilitate mounting on the compartment wall upper edges 46 and for receiving the bottom wall 22 of a further compartment stacked thereon.

In use, the compartments are stacked such that the lowermost compartment 20a is provided with the bottom wall 22 devoid of openings and a top wall 32 having the apertures 50, 52 therein aligned, respectively, with the conduit smaller openings 42, 44 disposed in the lowermost compartment 20a.

An upper compartment 20b (FIGS. 1 and 4) rests upon the lowermost compartment 20a, bottom edges 56 (FIG. 1) of the upper compartment 20b resting in, or snapping into, the grooves and/or ridges 54 on the top wall 32 of the lowermost compartment 20a.

Preferably, the assembly includes a second upper compartment 20c (FIG. 4) stacked on the upper compartment 20b.

Figure 3:
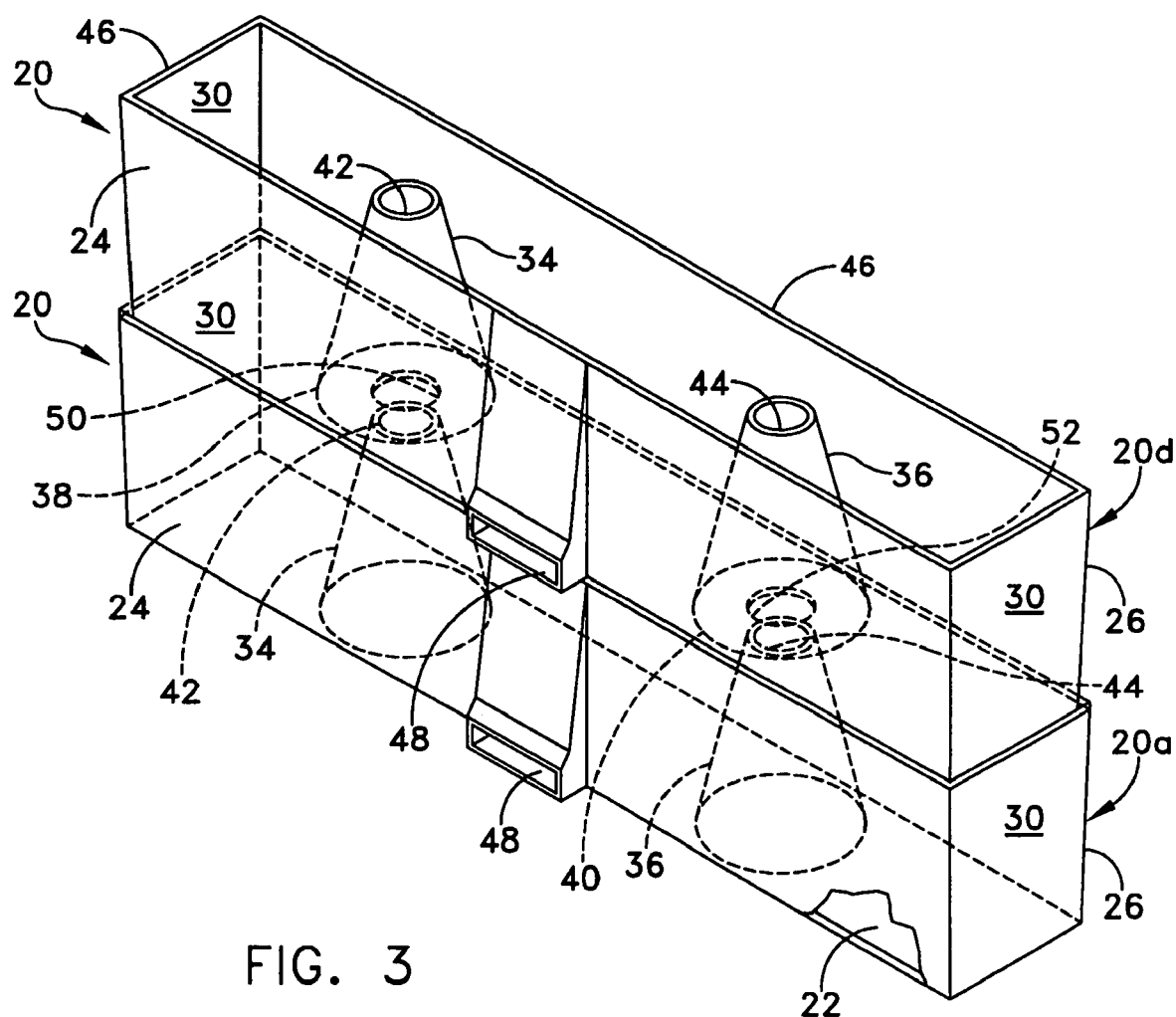
FIG. 3 is a diagrammatic perspective view of an upper compartment stacked upon a lower compartment to form a water storage and delivery assembly.
Figure 4:
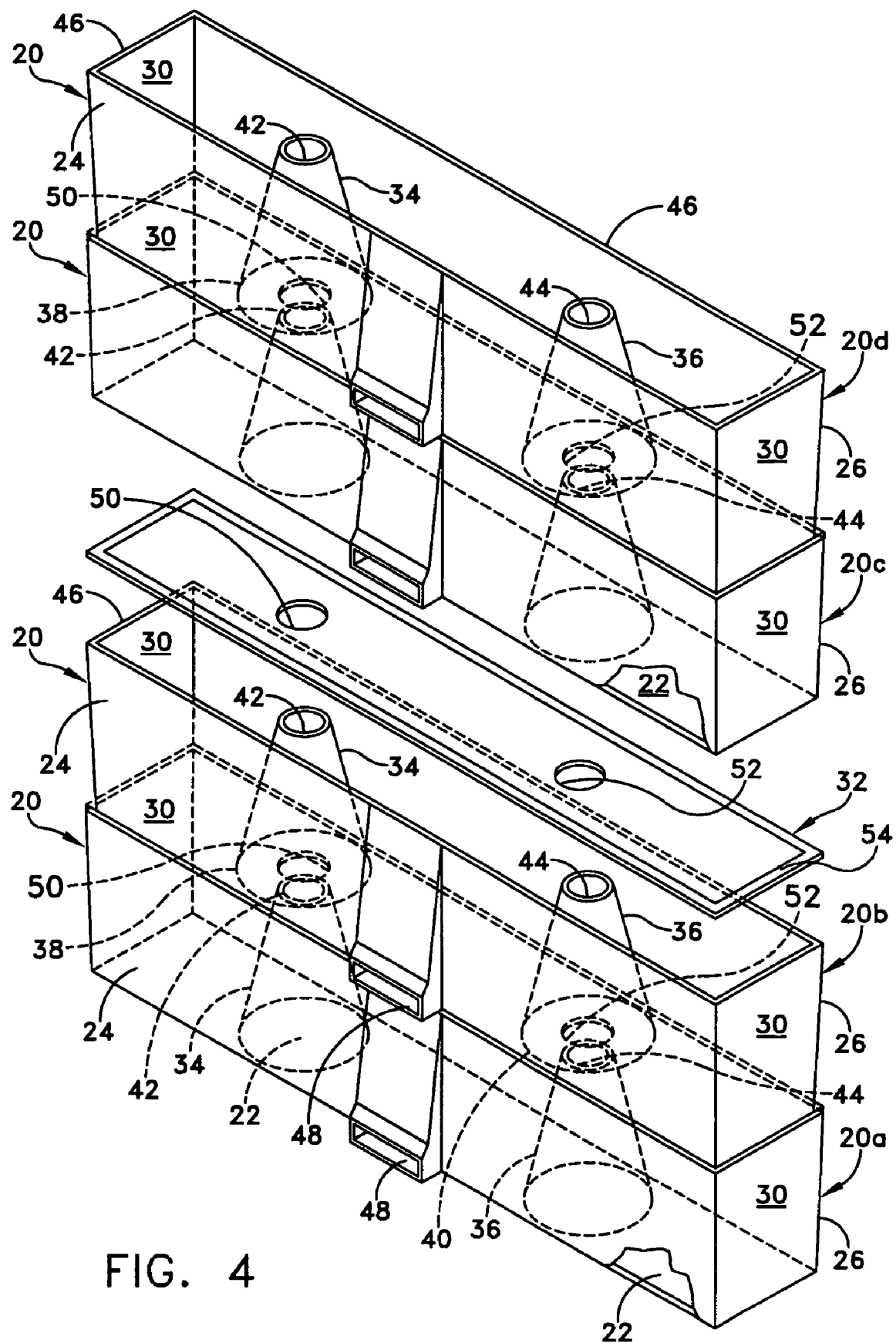
FIG. 4 is a perspective view of four stacked compartments, including upper and lower compartments and two intermediary compartments.

An uppermost compartment 20d (FIGS. 3 and 4) stacks upon the compartment(s) therebelow, one compartment 20a in FIG. 3, and three compartments 20a, 20b and 20c in FIG. 4, and is not provided with a top wall.

In operation, a stack of four compartments (FIG. 4) is generally used in cooperation with a stack of four exothermic chambers (not shown).

To prime the compartments 20, the uppermost compartment 20d is open topped, exposing the interior of the compartment 20d and the smaller conduit openings 42, 44 therein. Liquid is poured into the first 42 of the openings. The liquid flows through the opening 42, the conduit 34, the larger opening 38, the orifice 50 in the next lower compartment top wall, and through the conduits 34 thereunder until the liquid reaches the bottom wall 22 inside the larger end of the lowermost first conduit 34, whereupon the liquid fills the lowermost first conduit and overflows the smaller opening 42 thereof to start filling the lowermost compartment, while air displaced by the liquid escapes by way of the second conduit 36.

The liquid, in due course, fills the lowermost compartment 20a, including the interior of both conduits 34, 36, and begins to fill the next higher disposed container, and so on, until all the containers in the stack are filled.

The stack may be placed adjacent a similar stack of chambers housing magnesium-iron powder, or other exothermic material. The outlets 48 may be opened essentially simultaneously to activate four exothermic cells, or serially to activate one cell at a time.

When emptied, the assembly may be refilled for reuse.

There is thus provided a liquid storage and delivery system adapted to selectively deliver to associated exothermic chambers correct amounts of liquid to energize materials therein.

It will be understood that many additional changes in the details, materials, steps and arrangement of parts, which have been herein described and illustrated in order to explain the nature of the invention, may be made by those skilled in the art within the principles and scope of the invention as expressed in the appended claims.

What is claimed is:

1. A liquid storage and delivery assembly comprising:
   a plurality of stackable compartments, each of said compartments being provided with a planar bottom wall, opposed side walls, and opposed end walls;
   at least two frusto-conically shaped conduits mounted on the bottom planar wall of each of said compartments, the larger ends of said conduits being fixed to the planar bottom walls of said compartments;
   the bottom wall of a lowermost one of said compartments being closed, and the bottom walls of upper ones of said compartments having openings therein in communication with the larger ends of said conduits mounted in containers thereabove; whereby
   liquid admitted to a smaller end of a first of said conduits in an uppermost compartment is flowable therethrough to the first of said conduits in said lowermost compartment to overflow the lowermost compartment conduit and fill the lowermost compartment, with air escaping from the lowermost compartment through a second of said conduits;
   whereby the lowermost and upper compartments are thereby fillable with the liquid; and
   wherein said compartments are each provided with an outlet, said outlet being covered and being operable to permit the liquid to travel from each of said compartments.

2. The assembly in accordance with claim 1 wherein the assembly comprises four of said compartments stackably mounted one upon another, with said compartments being of the same cross-sectional area and general configuration.

3. A liquid storage and delivery assembly comprising;
   stackable compartments, each provided with a planar bottom wall, opposed side walls, and opposed end walls;
   first and second conduits mounted on the bottom planar wall of each of the compartments, bottom ends of said conduits being fixed to the planar bottom walls of said compartments;
   the bottom wall of a lower-most of said compartments being closed, and the bottom walls of other of said compartments having openings therein in communication with ends of said conduits; whereby
   liquid admitted to the first of said conduits in an upper-most compartment is flowable therethrough to the first conduit in lower stacked compartments to overflow the first conduits and fill said compartments lowermost upwardly, air escaping through the second conduit;
   whereby said compartments are sequentially filled with the liquid; and
   each of said compartments is provided with an outlet, said outlet being an opening, said opening being covered for retaining the liquid in the compartment, said outlet being operable to permit the liquid to travel from said compartments selectively substantially simultaneously and individually.

4. The assembly in accordance with claim 3 wherein each of said compartments other than the upper-most compartment is provided with a top wall.

5. The assembly in accordance with claim 4 wherein the uppermost of said compartments is open-topped and the top wall of each compartment thereunder is provided with apertures aligned with said conduits.

6. The assembly in accordance with claim 5 wherein each of said conduits comprises a frusto-conically shaped conduit.

7. The assembly in accordance with claim 6 wherein larger ends of said conduits are fixed to the bottom walls of said compartments, and smaller ends of said conduits are disposed proximate but spaced from a top plane of said compartments.

8. The assembly in accordance with claim 7 wherein the conduit smaller ends are aligned with the top wall apertures, respectively.

9. The assembly in accordance with claim 4 wherein the top walls are provided with structure to facilitate stacking of said compartments one on another.

10. The assembly in accordance with claim 9 wherein the structure comprises grooves in the top walls.

11. The assembly in accordance with claim 9 wherein the structure comprises ridges in the top walls.

12. The assembly in accordance with claim 8 wherein the conduit larger ends are in axial alignment with the conduit smaller ends and the top wall apertures.

* * * * *